United States Patent [19]
Auclair et al.

[11] Patent Number: 5,682,026
[45] Date of Patent: Oct. 28, 1997

[54] MULTIPLE CAROUSEL CARRIER AND CAROUSEL HANDLING MECHANISM

[75] Inventors: John M. Auclair, Seekonk; Joseph D. Antocci, Leominster, both of Mass.

[73] Assignee: Waters Investments Limited, Wilmington, Del.

[21] Appl. No.: 609,371

[22] Filed: Mar. 1, 1996

[51] Int. Cl.$^6$ .................................................. G06F 17/00
[52] U.S. Cl. ........................................... 235/375; 235/464
[58] Field of Search ..................................... 235/375, 464

[56] References Cited

U.S. PATENT DOCUMENTS 4,622,457  11/1986  Bradley et al. ........................ 235/375

*Primary Examiner*—Harold Pitts

[57] ABSTRACT

A sample handling mechanism including a direct drive carrier for positioning multiple trays or carousels of sample vials and a direct drive carousel handling mechanism that eliminates pulleys and belts and the problems associated therewith. The carousels handled by the sample handling mechanism are individually identifiable, stackable and include a viewing area for identifying and viewing the individual sample vials grouped in a respective carousel. The sample handling mechanism consists of two logical drive modules. A single center line or axis of rotation is effected in each of the drive modules. The two logical drive modules include a carrier mechanism that transports a plurality of sample carousels to a sampling station, and a carousel drive mechanism which engages a single carousel and presents the appropriate vial to be sampled. The carrier mechanism includes a multi-position spoke-like carrier portion that is driven by a single drive shaft coupled to a gear reduction stepper motor by a coupling. The carousel drive mechanism includes a linear actuator portion and a rotary actuator portion on a common center line or axis. The linear actuator portion effects engagement and disengagement of the rotary actuator portion with a properly positioned carousel, and includes a linear actuator stepper motor with a motor shaft attached to a lift housing. The lift housing holds the rotary actuator portion.

17 Claims, 8 Drawing Sheets

MULTIPLE CAROUSEL CARRIER AND CAROUSEL HANDLING MECHANISM

FIELD OF THE INVENTION

The present invention relates to autosampler mechanisms for use in automated sampling systems such as used at the front end of High Performance Liquid Chromatography (HPLC) systems, and more particularly to a sample handling system that includes a carrier for manipulating a plurality of carousels or trays of sample vials.

BACKGROUND OF THE INVENTION

Automated sampling systems are known for handling multiple sample sources, such as a tray with a plurality of vials with samples for processing in a liquid chromatography system. Generally, in such systems samples are stored in vials that are in turn stored on trays. The systems include transport facilities for transporting the sample vials to a sampling station, by positioning the trays under the sampling station and rotating the trays positioning each of the individual vials, one at a time, beneath the sampling station for sampling. Known systems typically involve a belt drive mechanism in the transport system.

For instance, U.S. Pat. No. 4,622,457 ("the 457 patent") describes an autosampler mechanism that positions a tray of sample vials beneath a sampling station and lifts each vial individually from the tray for sampling by a stationary sampling mechanism or needle. The sample vials are transported to and away from the sampling station by a transport system that includes a rotatable platter and four planetary trays carried by the rotatable platter.

A belt driven clutch and brake drive system described in the '457 patent facilitates rotation of the rotatable platter, and rotation of the trays relative to the rotatable platter so that any sample vial can be positioned beneath the sample station. The clutch and brake drive system requires an elaborate arrangement of drive shafts, pulleys and a drive belt to effect rotation of the platter and trays. A clutch electromagnet and an electromagnetic brake are also implemented in the '457 patent to effect three modes of operation: a braked mode wherein the tray mechanism is in a fixed, braked position; a platter rotation mode wherein the platter is rotated to rotate the four planetary trays in order to position a selected tray beneath the sampling station; and a tray rotation mode wherein the platter is fixed but the trays are rotated with respect to the platter.

Positioning of the sample vials in the '457 device is effected by an optical sensor located inside the sample compartment. Samples can be identified by slot location in the tray in accordance with "identifying elements" located under each slot. Each tray has an orientation spot located on its outer periphery for reading by the optical sensor. Location of the optical sensor(s) in the sample compartment presents a problem in that when the sample compartment is cooled moisture build-up can occur on the sensors and can cause the sensor to misread or not read at all.

Known systems such as disclosed in the '457 patent disadvantageously require lifting of the samples which unnecessarily agitates the sample vials. The elaborate clutch and pulley drive system disadvantageously requires many components that add significant cost to the system and take up significant amounts of space. The belt is subject to wear, misalignment and loosening over time which results in a need for frequent maintenance and repair. Furthermore, due to belt flexing and other mechanical phenomena, the belt and pulley system exerts unbalanced forces on the platter and trays which may cause inaccuracies in positioning and/or excessive vibration of the platter and trays resulting in further unnecessary agitation of the sample vials. Additionally, the expansion or reconfiguration of such a system by the addition of trays to a platter is extremely difficult and would likely exacerbate the disadvantages and problems described hereinabove, because a longer belt and additional pulleys would be required. Thus, the system of the '457 patent is seemingly limited in terms of sample capacity (to 80 samples: 4 trays times 20 samples per tray).

Other sample transport systems are known in the art, such as ones implemented in Model 712 and 717 Autosampler systems manufactured by Waters Chromatography (presently Waters Corporation), formerly a division of Millipore Corporation. Although free of the overly complex, costly and space consuming pulleys and clutch and brake mechanisms of some sample transport systems known in the art, the transport systems of the Model 712 and 717 Autosampler systems nonetheless incorporate belt driven actuators. Belt driven systems, as discussed, suffer disadvantages associated with the flexing and wear of the belt. Additionally, the Model 712 and 717 systems include an optical sensor located in the sample compartment for identifying the location of samples. Again, moisture build-up can occur on sensors located in the sample compartment which may cause the sensor to misread or to not read at all. Furthermore, the prior art Water's devices actuated a large, single carousel with a limited capacity of 48 or 96 sample vials.

SUMMARY OF THE INVENTION

The present invention provides a sample handling mechanism including a direct drive carrier for positioning multiple trays or carousels of sample vials and a direct drive carousel handling mechanism that eliminates pulleys and belts and the problems associated therewith.

The trays or carousels handled by the sample handling mechanism according to the invention are individually identifiable, stackable and include a viewing area for identifying and viewing the individual sample vials grouped in a respective carousel.

The sample handling mechanism according to the invention consists of two logical drive modules which are integrated into one assembly. A single center line or axis of rotation is effected in each of the drive modules. The two logical drive modules include a carrier mechanism that transports five sample carousels to a sampling station, and a carousel drive mechanism which engages a single carousel at the sampling station and presents the appropriate vial to be sampled.

The carrier mechanism includes a five-position spoke-like carrier portion that is driven by a single drive shaft coupled to a gear reduction stepper motor by a coupling. Carrier position is monitored by counting motor steps from a home position or a previous carousel position. Position is verified by an encoder wheel having five positional slots keyed and clamped directly to the drive shaft. Encoder slots are sensed by a dual channel optical interrupter in which one channel is for home verification, and the other is for carousel positional verification.

The carousel drive mechanism includes a linear actuator portion and a rotary actuator portion on a common center line or axis. The linear actuator portion effects engagement and disengagement of the rotary actuator portion with a properly positioned carousel, and includes a linear actuator stepper motor with a motor shaft attached to a lift housing.

The lift housing holds the rotary actuator portion including a rotary stepper motor, a concentric drive shaft, an encoder wheel attached to the drive shaft and position mechanisms that sense when the drive shaft is in an up position disengaged from a carousel or in a down position engaged with a carousel. The encoder wheel attached to the drive shaft is a twentyfour position encoder wheel, each position corresponding to the position of a sample vial in a carousel. The encoder is keyed and clamped for zero orientation of the shaft to the zero position of the encoder. The slots in the encoder wheel are sensed by a dual channel interrupter sensor wherein one channel is for verifying home and the other is for verifying individual vial positions. In accordance with the invention, the motor(s), encoder wheel, and optical sensor are all located outside the sample compartment.

Features of the invention include individual identification of each carousel within a carrier by a magnet placed in one of six unique locations which actuates a reed switch facilitating counting of steps from a "home" sensor to where the magnet is sensed. In contrast to prior art twelve inch carousels which are much larger and harder to store, carousels designed to be handled according to the invention are smaller and more compact, and are designed to be stackable, thus saving space, which is highly desirable particularly for refrigerated samples. The carousels include a viewing portion whereat a sample vial installed in the carousel is left exposed to allow a bar code label to be read by an optional bar code reader.

Keying of both the encoder wheel on the carrier drive shaft and the encoder wheel on the carousel drive shaft allows for ease of assembly and alignment. The carrier and its interface to a carrier drive shaft is designed with a "no tools" disengagement philosophy to allow the carrier to be manually removed for ease of cleaning the carrier and sample compartment. The multiple carousel carrier design provides the ability to add new or stat samples to the system simultaneously with ongoing vial sampling.

The carousel drive mechanism is configured to effect unidirectional rotation of the carousel to eliminate positional error due to backlash. The vertical motion of the lift housing portion of the drive mechanism is decoupled, i.e. it is not affected by the carousel rotary drive motion.

The sample handling mechanism increases the number of sample vials available for sampling from a typical maximum of 80 or 96, to a present maximum of 120 within substantially the same footprint. A flexible design has potential for extensibility by implementing alternative carriers and associated encoder and/or alternative carousels and associated encoder.

DESCRIPTION OF THE DRAWING

Other features and advantages of the present invention will become apparent from reading the following detailed description of an illustrative embodiment thereof, taken in conjunction with the drawing, in which.

DETAILED DESCRIPTION

Generally, the sample handling mechanism according to the invention and as illustrated in FIGS. 1–5, effects handling and actuation or transportation of samples contained in vials. The samples are "handled," or positioned proximate to a sampling station by the sample handling mechanism, for processing such as by HPLC apparatus, as known in the art. For high efficiency handling, the sample vials are grouped and maintained in individual carousels. The carousels (illustrated in FIGS. 1–3) are actuated first by a carrier mechanism (FIG. 5) which transports the carousels into position for rotation by a carousel drive mechanism (FIG. 6). The carousel drive mechanism in turn rotates each carousel, individually, to position the individual sample vials for sampling.

Carousels

Figure 1:
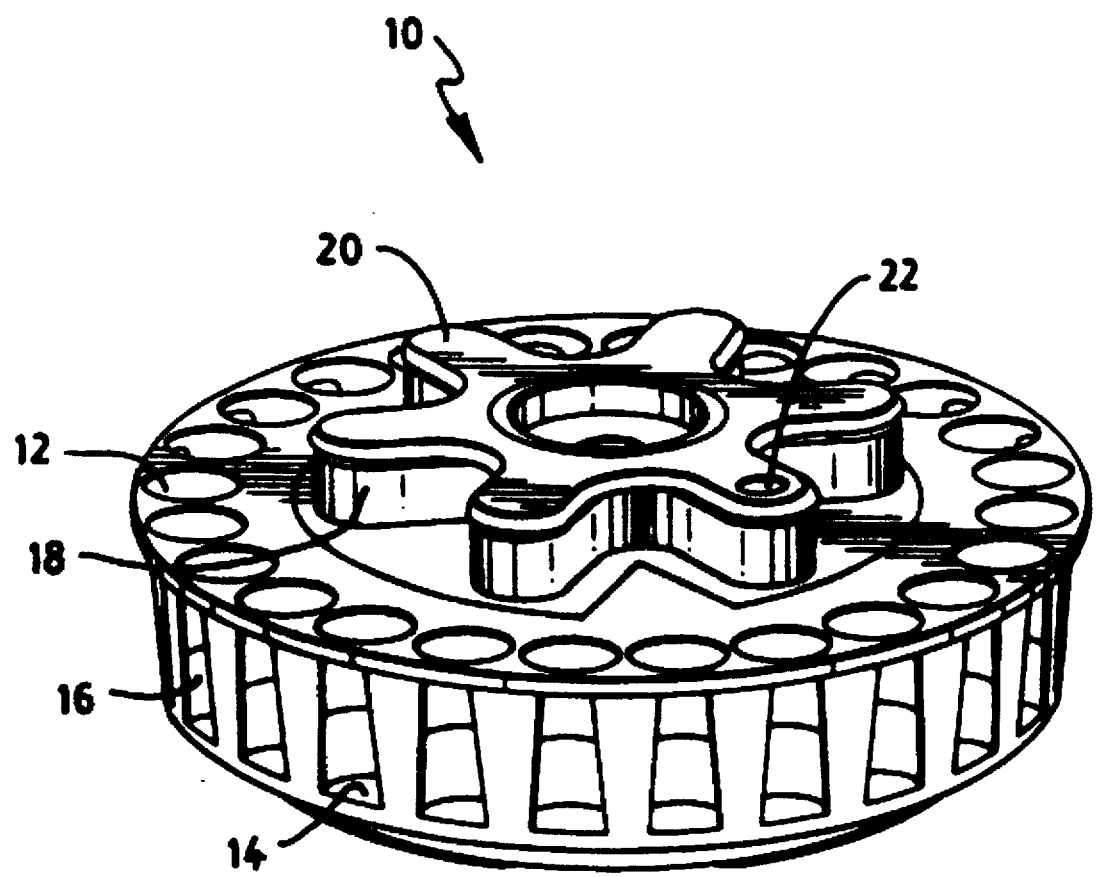
FIG. 1 is a perspective view of a carousel for use in a sample handling mechanism according to the invention.

As illustrated in FIG. 1, each carousel 10 is circular, approximately 5 inches in diameter, and includes twenty four vial positions 12 placed radially on an approximately 4.300 inch bolt circle. The vial positions are configured to receive virtually any 2 ml sample vial known in the art. The vials (not shown) fit loosely into the vial positions 12 to rest on a solid base 14 thereof. Each vial position 12 has a viewing window 16 to facilitate inspection, automated or otherwise, of identifying labels, e.g. bar coded labels, that identify the individual vials in the carousel 10.

In the present illustrative embodiment, the carousels 10 are a two piece plastic molded construction comprising a sample positioning portion 18 that is effectively the entirety of the carousel except for a spoke plate portion 20. The spoke plate portion 20 is a ⅛ inch thick plastic plate that caps off a spoke-shaped upper portion of the sample positioning portion 18. The spoke plate portion 20 includes a magnet receptacle 22 with a magnet installed therein, that works in conjunction with a reed switch proximate to the carousel drive mechanism 80, as described hereinafter, to facilitate simple, low cost, unique identification of the individual carousels.

Figure 2:
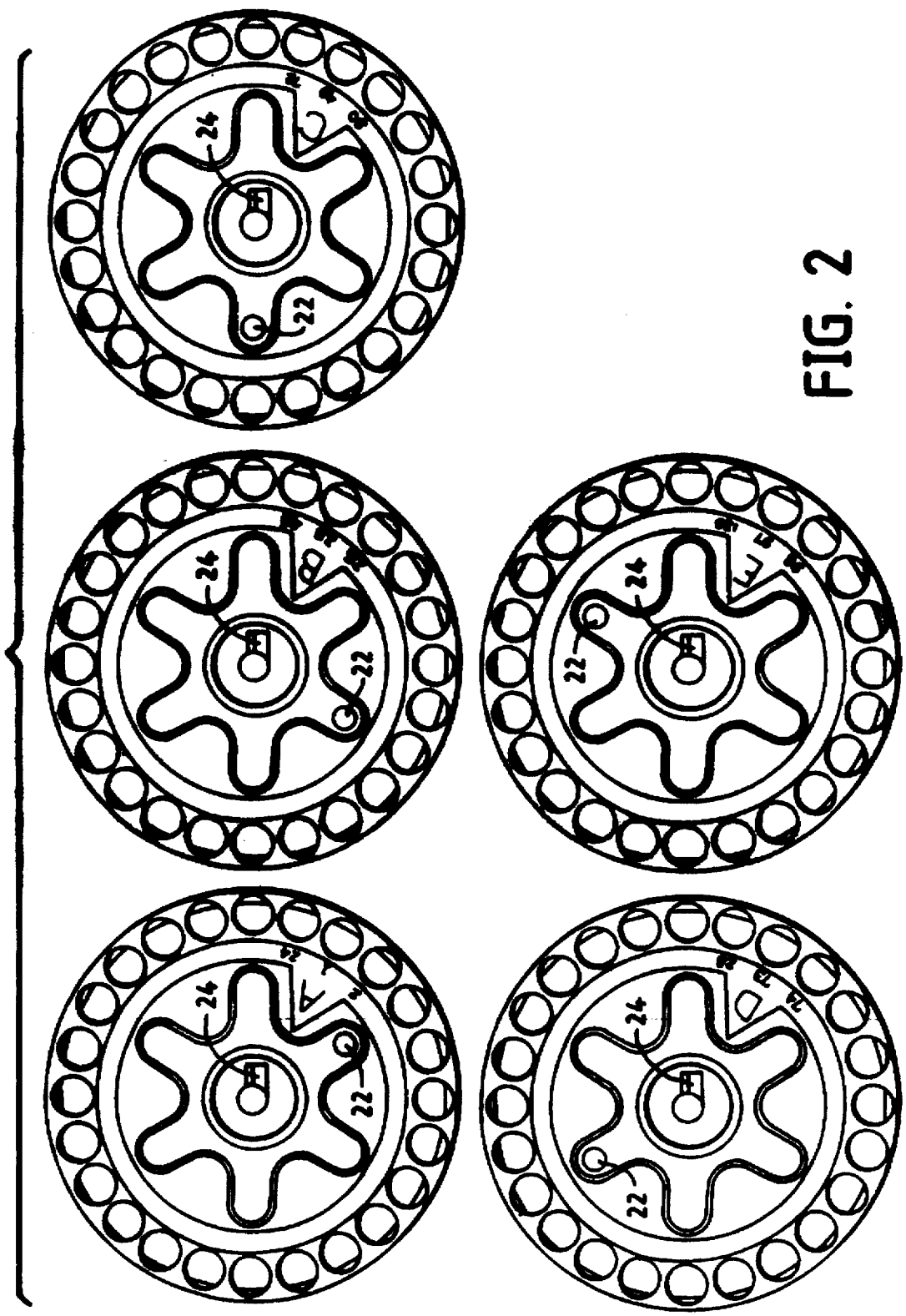
FIG. 2 is a top down view of a full complement of the carousels of FIG. 1.

As illustrated in FIG. 2, each one of a full complement of carousels handled, i.e. five carousels, is uniquely identifiable by locating the magnet receptacle 22 in one of six unique locations corresponding with six spokes on the spoke plate portion 20. The unique location, and corresponding unique identification, is defined by the location of the magnet receptacle 22 with respect to a drive pin slot 24 located in a recess at the center of the spoke plate portion 20. A full complement of carousels has vial sample locations that are uniquely identifiable and successively numbered between 1 and 120.

Figure 3:
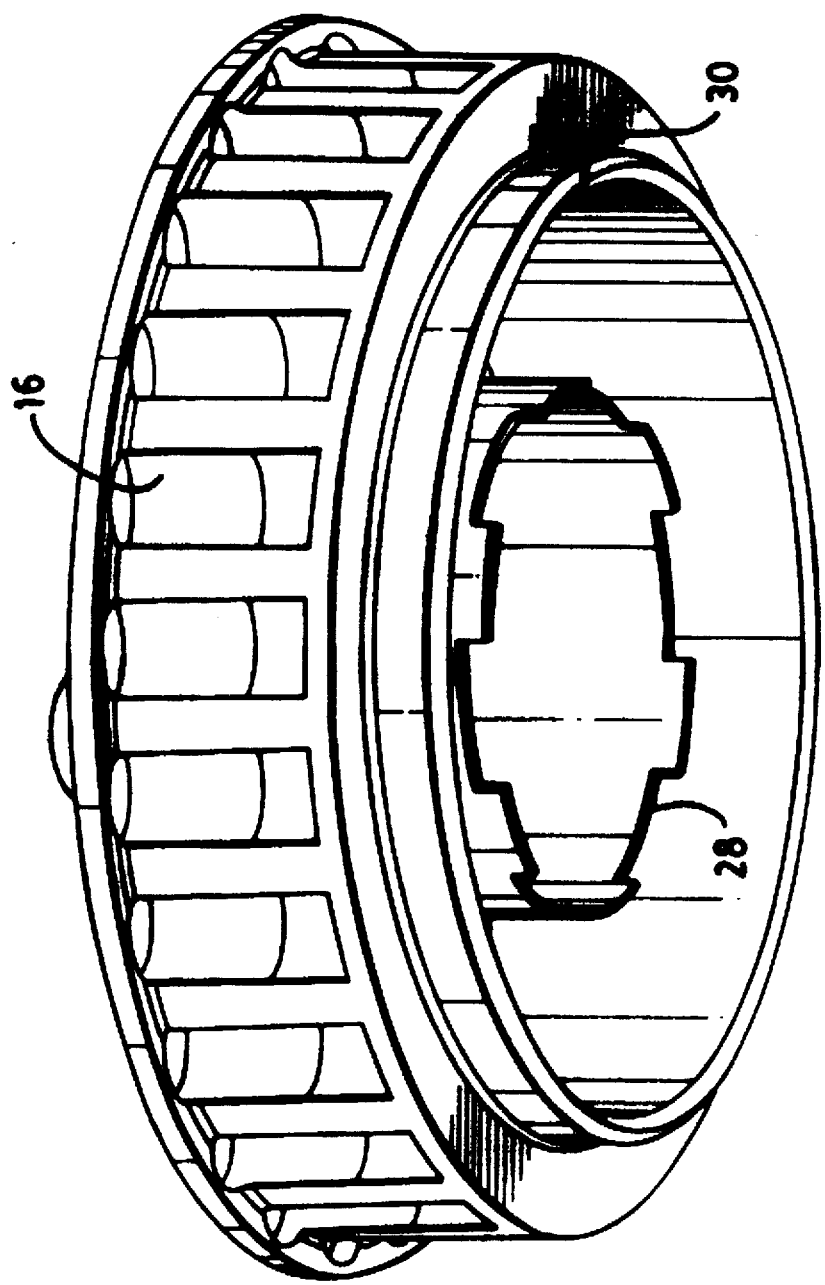
FIG. 3 is a perspective view of a bottom of the carousel of FIG. 1.

The spoke-shaped upper portion of the sample positioning portion 18 is configured to engage a plurality of cut-outs 28 on the bottom of the carousels 10, as illustrated in FIG. 3, to facilitate stacking of the carousels for compact storage when not in use. A circular bottom ridge 30 has a circumference just slightly larger than a circumference circumscribing the six spokes of the spoke-shaped upper portion of the sample positioning portion 18 to further ensure stable stacking of the carousels.

In use, the full complement of carousels is manipulated into position with respect to a sample handling station by a sample handling mechanism according to the invention.

Sample Handling Mechanism

Referring now to FIGS. 4–6A, the sample handling mechanism 40 transporting carousels according to the invention consists of two logical drive modules which are integrated into one assembly or frame 42. A carrier mechanism 50 is a first drive module, that transports five sample carousels 10 to a sampling station (not shown), as required. A second drive module is a carousel drive mechanism 80 which engages a single carousel proximate to the sampling station and presents an appropriate vial to the sampling station as programmed and as understood by those skilled in the art.

Carrier Mechanism

Figure 4:
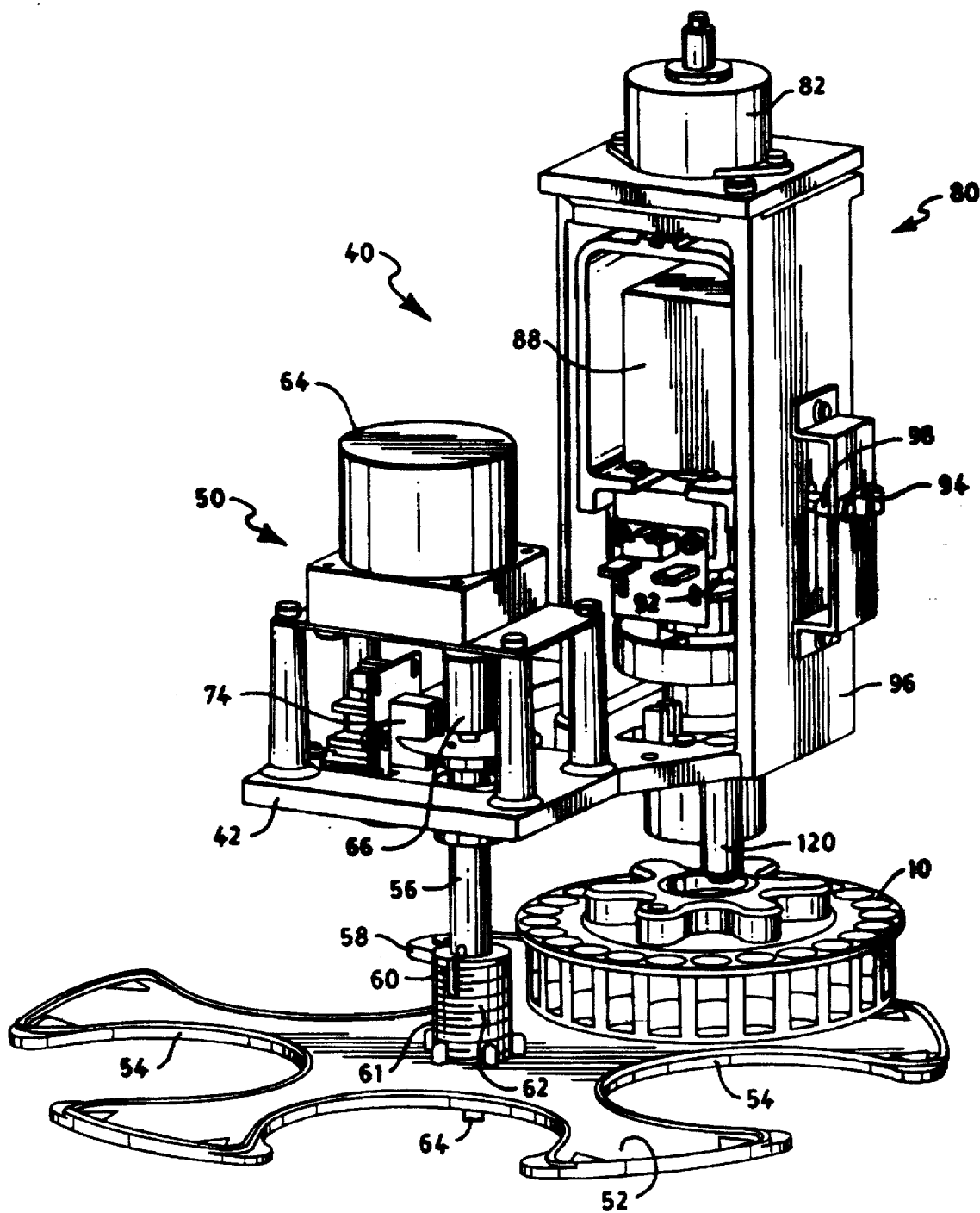
FIG. 4 is a perspective view of a sample mechanism according to the invention including a carrier mechanism and a carousel drive mechanism.
Figure 5:
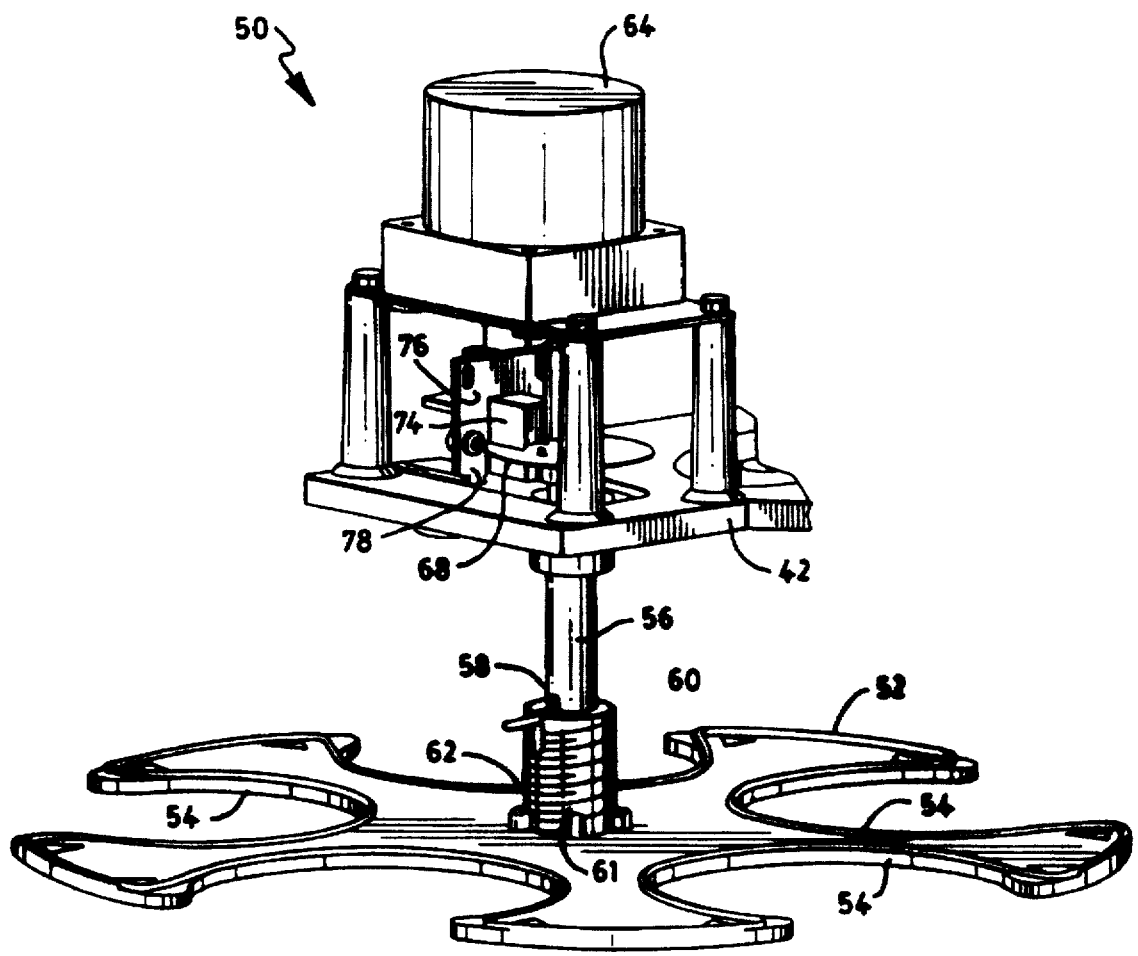
FIG. 5 is a perspective view of a carrier mechanism of FIG. 4.
Figure 5A:
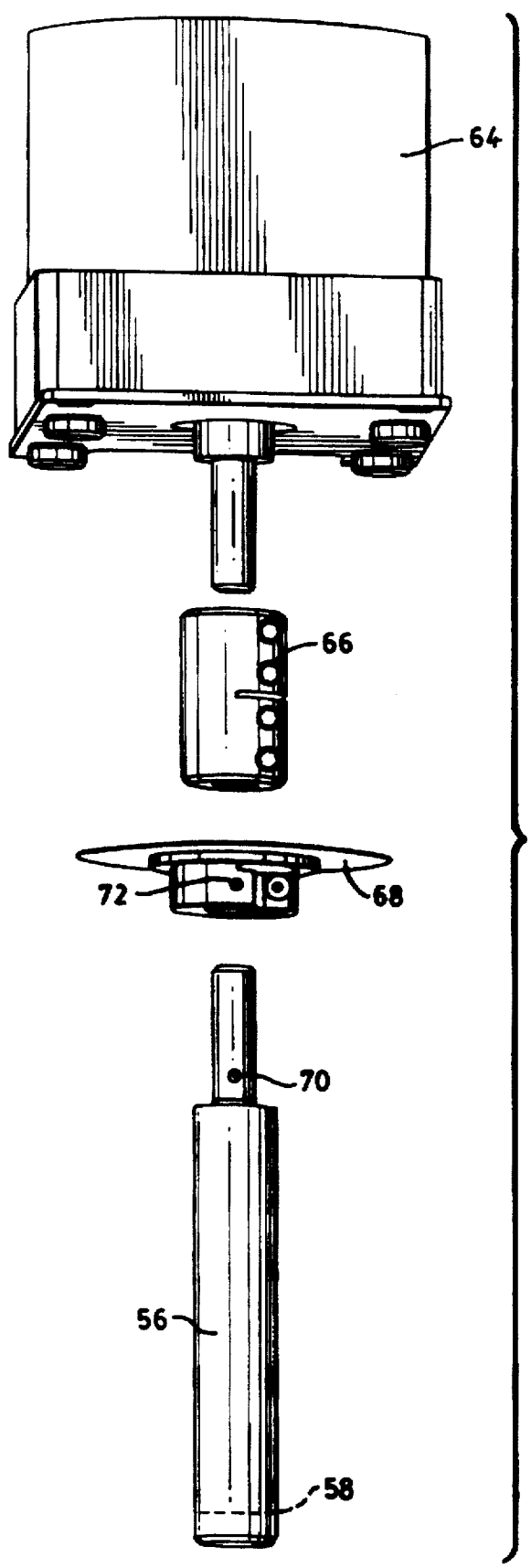
FIG. 5A is an exploded view of a carrier drive shaft assembly of the carrier mechanism of FIGS. 4 and 5.
Figure 6:
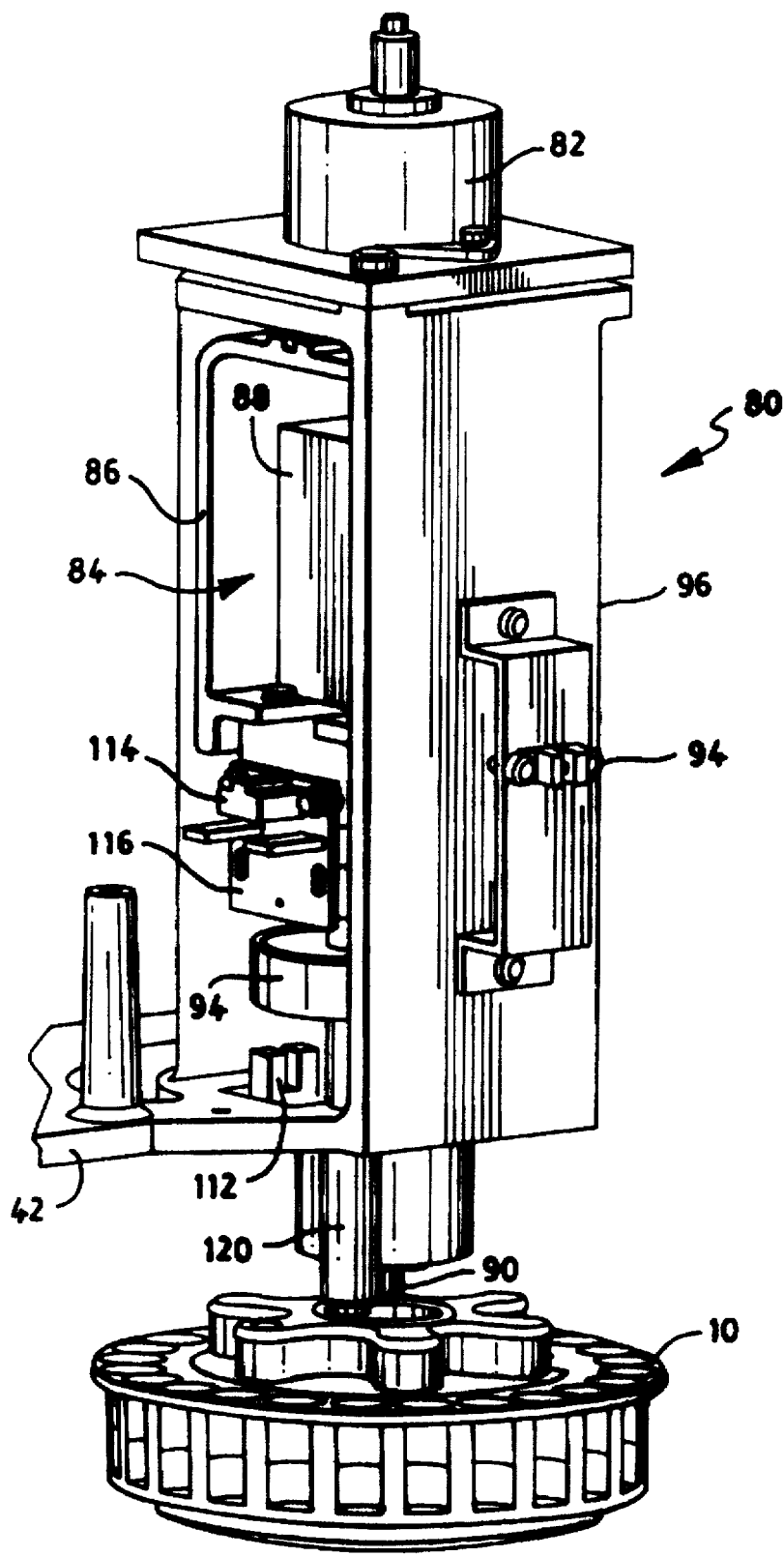
FIG. 6 is a perspective view of a carousel drive mechanism of FIG. 4.

Referring now to FIGS. 4, 5 and 5A, the carousels 10 are installed by an operator in an appropriate location of a carrier 52. Preferably, the operator installs the set of carousels in the carrier so that successively numbered carousels are adjacent to one another. The carrier 52 is a five-position spoke-like part that has partial-circumference positions 54 for each of five carousels comprising a full complement with sample vial positions numbered 1–120. Carousels 10 fit removably into respective positions such that the circular bottom ridge 30 of a carousel 10 is snugly embraced by a respective one of the partial-circumference positions 54 to retain the carousel in the carrier 52.

The carrier 52 is driven by a single drive shaft 56 which it engages with and disengages from in accordance with a "no tools" disengagement philosophy. That is, the carrier can be easily, manually removed to facilitate ease of cleaning a sample compartment (not shown) in which the carrier resides. Accordingly, the carrier drive shaft 56 has a drive slot 58 in an engagement end thereof. The carrier 52 has a spring-loaded key pin 60 passing through a spring housing 62. A spring 61 is disposed about the spring housing. The spring housing 62 has an open portion (not shown) or cut-out that is sufficient to provide clearance for the drive shaft 56 and permits the carrier to be moved horizontally, to engage and disengage the carrier and carrier drive shaft 56. The key pin 60 is biased outwardly from the carrier 52 to engage the slot 58 in the carrier drive shaft 56 when the carrier is disposed on a bearing surface in the sample compartment. In the present illustrative embodiment, the carrier includes a boss 64 on a bottom surface thereof which engages a flat bearing surface in the sample compartment.

Disengagement of the carrier 52 is effected manually by an operator by depressing the spring loaded key pin 60, and pulling the carrier 52 toward the operator to disengage the carrier 52 from the drive shaft 56, when the carrier is in a "home" position, i.e. the open portion on the spring housing is facing away from the operator and the carrier can be moved horizontally toward the front of the sample compartment.

The carrier drive shaft 56 is coupled to a carrier rotary gear reduction stepper motor 64 by a coupling 66, best seen in FIG. 5A. The carrier stepper motor 64 is configured so that the carrier 52 rotates counter clockwise only, to eliminate any backlash due to the gear reduced stepper drive. The carrier 52 is positioned by the motor 64 by counting motor steps from the home position or a previous carousel position. This position is verified by an encoder wheel 68 keyed and clamped directly to the carrier drive shaft 56. The encoder wheel 68 is mounted proximate to the coupling 66 which is at an end of the carrier drive shaft 56 distal to the drive slot 58.

The encoder wheel 68 has five positional slots to correspond to the positions of the five carousels in the carrier 52. The encoder wheel 68 is used to verify each of the five positions. One of the slots in the encoder wheel is elongated and acts as the home or "A" position to correspond to the position whereat a first carousel of a full complement (i.e. the A carousel with vials 1–24) is located toward the front of the sample compartment and whereat the carrier can be removed by releasing the spring-loaded key pin 60 and moving the carrier horizontally toward the operator as discussed hereinbefore. The encoder wheel 68 is keyed to the carrier drive shaft by a hole 70 in the carrier drive shaft 56 that mates with an alignment key hole 72 on the encoder wheel assembly 68. Keying the encoder wheel 68 ensures a positional orientation of the drive slot 58 in the end of the carrier drive shaft 58 that corresponds to the home position on the encoder wheel. Keying also facilitates ease of assembly.

The slots on the encoder wheel 68 corresponding to the carrier positions are sensed by a dual channel optical interrupter or sensor 74. One channel of the optical interrupter is for home verification, and the other for carousel positional verification. The sensor 74 is mounted directly on a circuit board 76 which is in turn mounted on brackets 78 that are attached to the frame 42 in a manner allowing only one degree of freedom, to facilitate ease of adjustment. The carrier stepper motor 64, encoder wheel 68, and sensor 74, are all disposed in positions outside of the sample compartment.

Once a carousel 10 is positioned under the sampling station (not shown), by the carrier mechanism 50 as discussed in detail hereinbefore, it can be engaged for positioning by the carousel drive mechanism 80.

Carousel Drive Mechanism

Figure 6A:
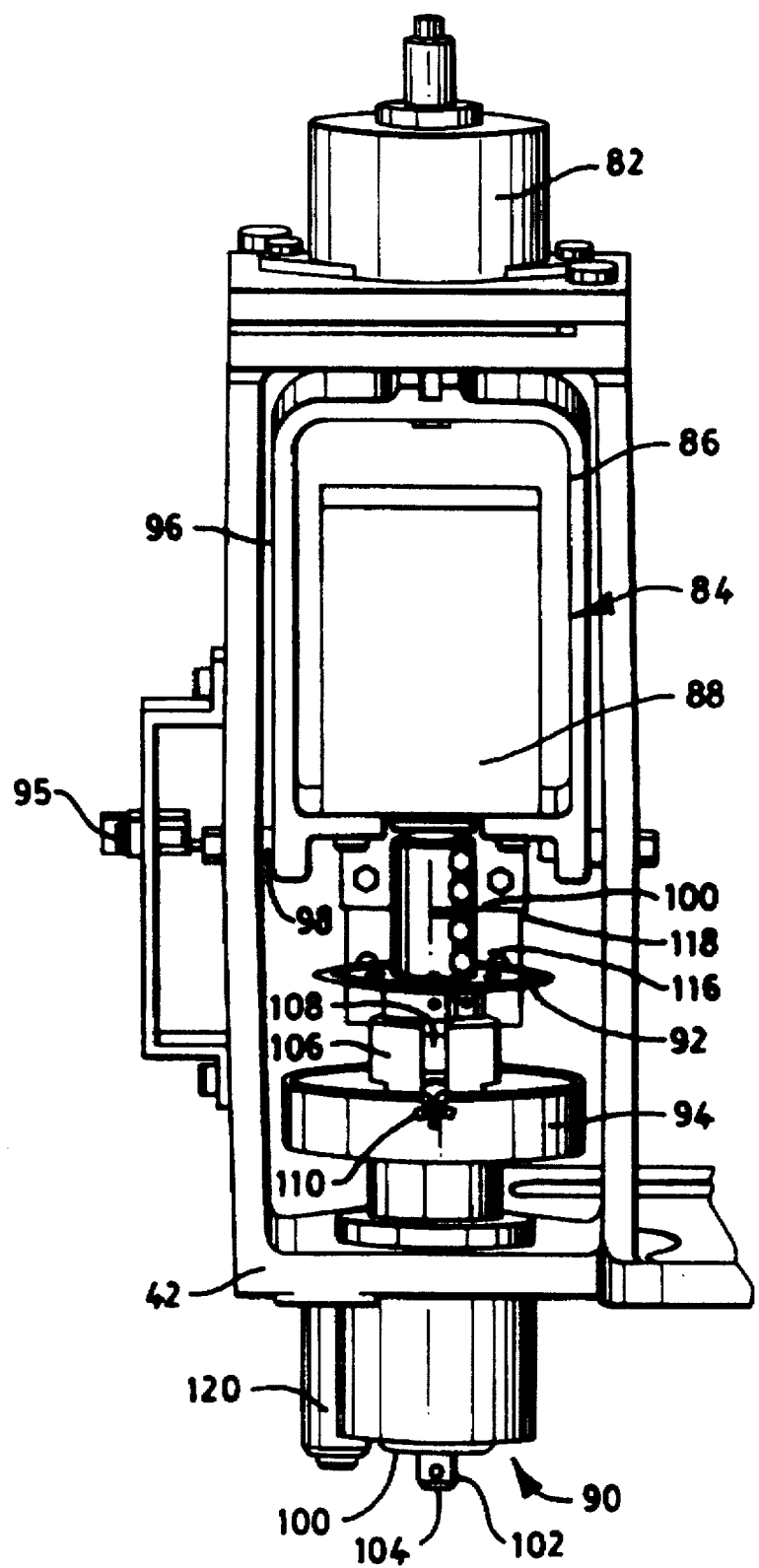
FIG. 6A is a side view of the carousel drive mechanism of FIGS. 4 and 6.

Referring now to FIGS. 4, 6 and 6A, the carousel drive mechanism 80 is comprised of a linear actuator drive motor 82 which drives a rotary motion carousel drive mechanism 84 up and down in a linear manner. The rotary motion carousel drive mechanism 84 is comprised of a lift housing 86 that houses a rotary gear reduction stepper motor 88 attached a keyed concentric carousel drive shaft 90. The keyed carousel drive shaft 90 has attached thereto a carousel positioning encoder wheel 92 (best seen in FIG. 6A), for verifying rotary position of the carousel 10 engaged by the carousel drive shaft 90. The carousel drive shaft also has engaged thereto an optical fence 94, as described hereinafter.

Controlled linear positioning, in a vertical plane, of the rotary motion carousel drive mechanism 84 is effected by counting linear actuator drive motor 82 motor steps as the lift housing 86 is actuated up and down. Motor steps are counted in a plus or minus direction from a zero position sensed by an optical interrupter sensor 95 mounted on the outside of an exterior housing 96. The exterior housing 96 incorporates, among other things, the rotary motion carousel drive mechanism 84, the carousel positioning encoder wheel 92, substantial portions of the carousel drive shaft 90, and the optical fence 94. The rotary motion carousel drive mechanism 84 is driven up and down in a linear manner to effect engagement (lift housing 86 down) and disengagement (lift housing 86 up) of a carousel by portions of the carousel drive shaft 90, as described hereinafter. The zero position of the linear actuator drive motor 82 driving the rotary motion carousel drive mechanism 84 is sensed when a beam of the optical interrupter sensor 94 is broken by an optical flag incorporated in an anti-rotation pin 98 (best seen in FIGS. 4 and 6A) mounted in a side of the lift housing 86.

The carousel drive shaft 90 is actuated linearly with the lift housing 86, as it is coupled, via a coupling 100, to a shaft of the rotary stepper motor 88 incorporated in the lift housing 86 and lifted by the linear motor 82. The carousel drive shaft 90 is comprised of a spring loaded internal shaft 102 (best seen in FIG. 6A), with a fixed drive pin 104 on an exposed end. The fixed drive pin 104 is configured to engage in the drive pin slot 24 (FIG. 2), located in the recess at the center of the spoke plate portion 20 in each carousel 10.

At the other end of the internal shaft 102 is a threaded hole (not shown) substantially in alignment with the fixed drive pin 104. The spring loaded internal shaft 102 is disposed within an external shaft 106 that has a longitudinal slot 108 therein. The threaded hole on the internal shaft 102 and the fixed drive pin 104 at the exposed end of the internal drive shaft 102 are aligned with the longitudinal slot 108 in the external shaft 106. A floating key 110 is attached at the threaded hole of the internal shaft 102 once the internal shaft is mounted into the external shaft 106. The floating key 110 has the optical fence 94 attached thereto so that as the floating key 110 moves up and down with the spring loaded internal shaft 102, so does the optical fence 94.

When the rotary motion carousel drive mechanism 84 is actuated downward in a controlled manner, the spring loaded internal drive shaft 102 is actuated downward. The fixed drive pin 104 at the exposed end of the internal drive shaft is thus positioned to enter the drive pin slot 24 (FIG. 2), located in the recess at the center of the spoke plate portion 20 in the carousel, assuming that the carousel is appropriately positioned. With the drive shaft actuated downwardly and the fixed drive pin 104 engaged in the drive pin slot 24, the optical fence 94 breaks a beam on an optical sensor 112 (best seen in FIG. 6) mounted on the frame 42. Accordingly, the optical sensor 112 provides an indication to the system that the fixed drive pin 104 is engaged in the drive pin slot 24 in the carousel.

Position of the carousel drive shaft 90 is a function of the encoder wheel 92 attached on the coupling end of the shaft. The carousel position encoder wheel is a 24 position wheel, each position corresponding to a sample vial location in a carousel as described hereinbefore. As in the carrier drive shaft, the encoder on the carousel drive shaft is keyed and clamped for zero orientation of the shaft to the zero position of the encoder. The slots in the encoder wheel 92 are sensed by a dual channel interrupt sensor 114 (best seen in FIG. 6). As in the carrier drive, one channel is for verifying home and the other is for verifying individual vial positions. The sensor 114 is mounted directly on a circuit board 116 which is in turn mounted on brackets 118 that are attached to the frame 42 in a manner allowing only one degree of freedom, to facilitate ease of adjustment.

Carousel identification is effected at the carousel drive mechanism 80 by the magnet receptacle 22 with a magnet installed in one of six unique locations corresponding with six spokes on the spoke plate portion 20 as described hereinbefore. The magnet works in conjunction with a reed switch (not shown) installed in a reed switch holder 120 on the frame 42 proximate to the carousel drive mechanism 80. The number of carrier stepper motor 64 steps from home are tracked and when the magnet is located by the reed switch the identification of the particular carousel can be determined by the position of the magnet relative to the home position.

With the appropriate control mechanisms, which are not within the scope of the present disclosure, each of 120 vial positions in the five carousels of a full complement handled by the carrier, can be accessed or positioned in an identifiable manner, in several modes, by the sample handling mechanism described.

Although a five position encoder wheel is used in the carrier mechanism and a 24 position encoder wheel is used in the carousel actuator portion described hereinbefore, it will be appreciated that according to the flexible and extensible design described herein, greater or fewer positions can be implemented on the respective encoder wheels to effect alternative implementations with greater or fewer carrier carousel positions and/or greater or fewer carousel sample vial positions.

While the carousels described herein are of a two piece construction configured to be handled by a carrier that is a five-position spoke-like part, it should be appreciated that the carrier mechanism and carousel drive mechanism can be substantially similarly implemented to handle other types of carousels, and vice versa. The carrier can be implemented to handle carousels with a different mechanism than the partial circumference part disclosed.

Although the carrier described herein includes a boss 64 on a bottom surface thereof which engages a flat bearing surface in the sample compartment it will be appreciated that other bearings, such as ball or roller bearings or the like could be implemented.

Although the invention has been shown and described herein with respect to an illustrative embodiment thereof, it will be appreciated that the foregoing and various other changes, omissions and additions in the form and detail thereof may be made therein without departing from the spirit and scope of the invention.

What is claimed is:

1. A sample handling apparatus for handling multiple trays of sample vials, comprising:

a carrier mechanism having a first axis of rotation and comprising a tray carrier portion, a carrier actuator portion and a first interface portion interfacing said tray carrier portion into engagement with said carrier actuator portion, said tray carrier portion receiving said multiple trays and said actuator portion actuating said multiple trays substantially simultaneously in a rotary manner about said first axis of rotation; and a tray drive proximate to said carrier mechanism, said tray drive having a tray actuator with a second axis of rotation, said tray actuator having a tray interface portion configured to engage with and disengage from, individually, each of said multiple trays in said tray carrier portion of said carrier mechanism and said tray interface configured to actuate each of said multiple trays individually about said second axis of rotation when engaged with an individual one of said multiple trays.

2. The apparatus of claim 1 wherein said carrier actuator portion includes a carrier drive shaft and said first interface portion interfacing said tray carrier portion to said carrier actuator portion comprises a slot in said carrier drive shaft and an engagement housing on said tray carrier portion including a pin disposed therethrough and a spring biasing said pin into engagement with said slot.

3. The apparatus of claim 2 wherein said spring is disposed on the outside of said engagement housing on said tray carrier portion which includes a clearance section having a dimension greater than a diameter of said carrier drive shaft proximate to said slot and wherein said pin disposed through said engagement housing is actuatable to compress said spring and said tray carrier portion is actuatable in a horizontal manner for said clearance section to clear said carrier drive shaft to remove said tray carrier portion from engagement with said carrier actuator portion.

4. The apparatus of claim 1 wherein said tray carrier portion receiving said multiple trays comprises a five position spoke-shaped part having a seating position for seating five sample vial trays therein.

5. The apparatus of claim 1 wherein said actuator portion actuating said multiple trays substantially simultaneously in a rotary manner about said first axis of rotation comprises a rotary motor having a shaft attached thereto, said first axis of rotation being about said shaft, said shaft having an encoder attached thereto defining a plurality of positions each one of said plurality of positions corresponding to a respective one of said multiple trays.

6. The apparatus of claim 5 further including an optical sensor associated with said encoder to sense each one of said plurality of positions.

7. The apparatus of claim 1 wherein said tray carrier portion carries a plurality of trays, each of said plurality of trays comprising an upper portion and a lower portion, said upper portion having a plurality of protuberances and said lower portion having a plurality of cut-outs configured to receive said plurality of protuberances from another one of said plurality of trays to stack said plurality of trays.

8. The apparatus of claim 7 wherein at least one of said plurality of protuberances has an identifying mechanism to provide unique identification for each one of said plurality of trays.

9. The apparatus of claim 8 wherein said identifying mechanism is a magnet in a recess.

10. The apparatus of claim 1 wherein said tray drive comprises a linear actuator and a rotary actuator having a shaft with a first end and a second end, said second end of said shaft having said tray interface portion disposed thereat, said linear actuator being configured to linearly actuate said rotary actuator along said second axis of rotation between a first position in which said tray interface portion engages an individual tray and a second position in which said tray interface portion is disengaged from said individual tray, said rotary actuator configured to effect rotation of said individual tray about said second axis of rotation when in said first position.

11. The apparatus of claim 10 wherein said shaft has an encoder disposed proximate to said first end for determining a position of said individual tray.

12. The apparatus of claim 10 further including a sensor for determining a position of said linear actuator.

13. The apparatus of claim 12 wherein said rotary actuator is disposed in a housing that is also actuated by said linear actuator, and said sensor is an optical sensor disposed to read an optical indicator on said housing.

14. The apparatus of claim 10 wherein said shaft comprises an exterior shaft and an interior shaft disposed in a spring-loaded manner in said exterior shaft, a second end of said interior shaft comprises said second end of said shaft having said tray interface portion disposed thereat, and a first end of said interior shaft includes a member that extends outwardly protruding from said exterior shaft and includes a position indicator thereon, said position indicator being in a first state when said tray interface portion engages an individual tray to effect rotation of said individual tray about said second axis of rotation, and said position indicator being in a second state when said tray interface portion is disengaged from said individual tray.

15. The apparatus of claim 14 wherein said position indicator is an optical fence that engages an optical sensor when said tray interface portion engages an individual tray to effect rotation of said individual tray about said second axis of rotation, said optical fence being disengaged from said optical sensor when said tray interface portion is disengaged from said individual tray.

16. A tray carrier mechanism having a first axis of rotation about which a plurality of trays are rotated, comprising:

a tray carrier portion receiving said plurality of trays, said tray carrier portion including an engagement housing on said tray carrier portion including a pin disposed therethrough and a spring biasing said pin;

a carrier actuator portion actuating said plurality of trays substantially simultaneously in a rotary manner about said first axis of rotation, said carrier actuator portion including a carrier drive shaft having a slot disposed in an end thereof, wherein said tray carrier portion is interfaced to said carrier actuator portion by said pin being biased into engagement with said slot.

17. A tray drive mechanism comprising: a linear actuator and a rotary actuator having a shaft with a first end and a second end and defining an axis of rotation, said second end of said shaft having a tray interface portion disposed thereat for periodically interfacing with a tray to be driven, said linear actuator being configured to linearly actuate said rotary actuator along said axis of rotation between a first position in which said tray interface portion engages said tray to be driven and a second position in which said tray interface portion is disengaged from said tray to be driven, said rotary actuator configured to effect rotation of said tray about said axis of rotation when in said first position.

* * * * *